US00PP33841P3

(12) United States Plant Patent
Perrault et al.

(10) Patent No.: US PP33,841 P3
(45) Date of Patent: Jan. 11, 2022

(54) HOP PLANT NAMED 'HBC 695'

(50) Latin Name: *Humulus lupulus*
Varietal Denomination: HBC 695

(71) Applicant: HOP BREEDING COMPANY, L.L.C., Yakima, WA (US)

(72) Inventors: Jason Perrault, Toppenish, WA (US); Eugene G. Probasco, Yakima, WA (US); Michael D. Ferguson, Yakima, WA (US); Scott Varnum, Ellensburg, WA (US); Jaime Avalos P., Granger, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 16/974,192

(22) Filed: Nov. 6, 2020

(65) Prior Publication Data

US 2021/0329823 P1 Oct. 21, 2021

Related U.S. Application Data

(60) Provisional application No. 63/101,090, filed on Apr. 15, 2020.

(51) Int. Cl.
*A01H 5/02* (2018.01)
*A01H 6/00* (2018.01)
*A01H 6/28* (2018.01)

(52) U.S. Cl.
USPC ..... Plt./236
CPC ..... *A01H 6/00* (2018.05); *A01H 6/28* (2018.05)

(58) Field of Classification Search
USPC ..... Plt./236
CPC ..... A01H 6/28; A01H 5/02
See application file for complete search history.

*Primary Examiner* — Keith O. Robinson
(74) *Attorney, Agent, or Firm* — Svendsen Legal, LLC

(57) ABSTRACT

A new hop plant named 'HBC 695' is disclosed. 'HBC 695' is used for its exceptional and unique aromatic qualities, and is suitable for beer flavoring.

6 Drawing Sheets

Genus and species: *Humulus lupulus*.
Variety denomination: 'HBC 695'.

STATEMENT REGARDING FEDERALLY SPONSORED RESEARCH OR DEVELOPMENT

None

BACKGROUND OF THE INVENTION

HBC '695' is a product of a controlled breeding program carried out by the inventors in the Yakima Valley of Washington State. 'HBC 695' was one of several seedlings resulting from a controlled cross made in 2009 with female parent 'HBC 466', an unpatented variety, and male parent '06-019 (25-12-03)', which is also unpatented. Seedling plants from this cross were planted in 2010 and screened for disease resistance and sex in a greenhouse and field nursery near Toppenish, Wash. A single plant of 'HBC 695' was selected in 2013. In 2014 'HBC 695' was asexually reproduced via softwood cuttings, and expanded to thirty (30) plants in an evaluation block near Toppenish, Wash. In 2019 'HBC 695' was further expanded to a one (1) acre test block near Toppenish, Wash. with plants asexually reproduced via softwood cuttings. The 'HBC 695' plants have now been observed and evaluated for several years. Throughout several generations of asexual propagation, 'HBC 695' has been observed to retain its distinctive characteristics and remain true to type.

BRIEF DESCRIPTION OF THE PHOTOGRAPHS

Figure 1:
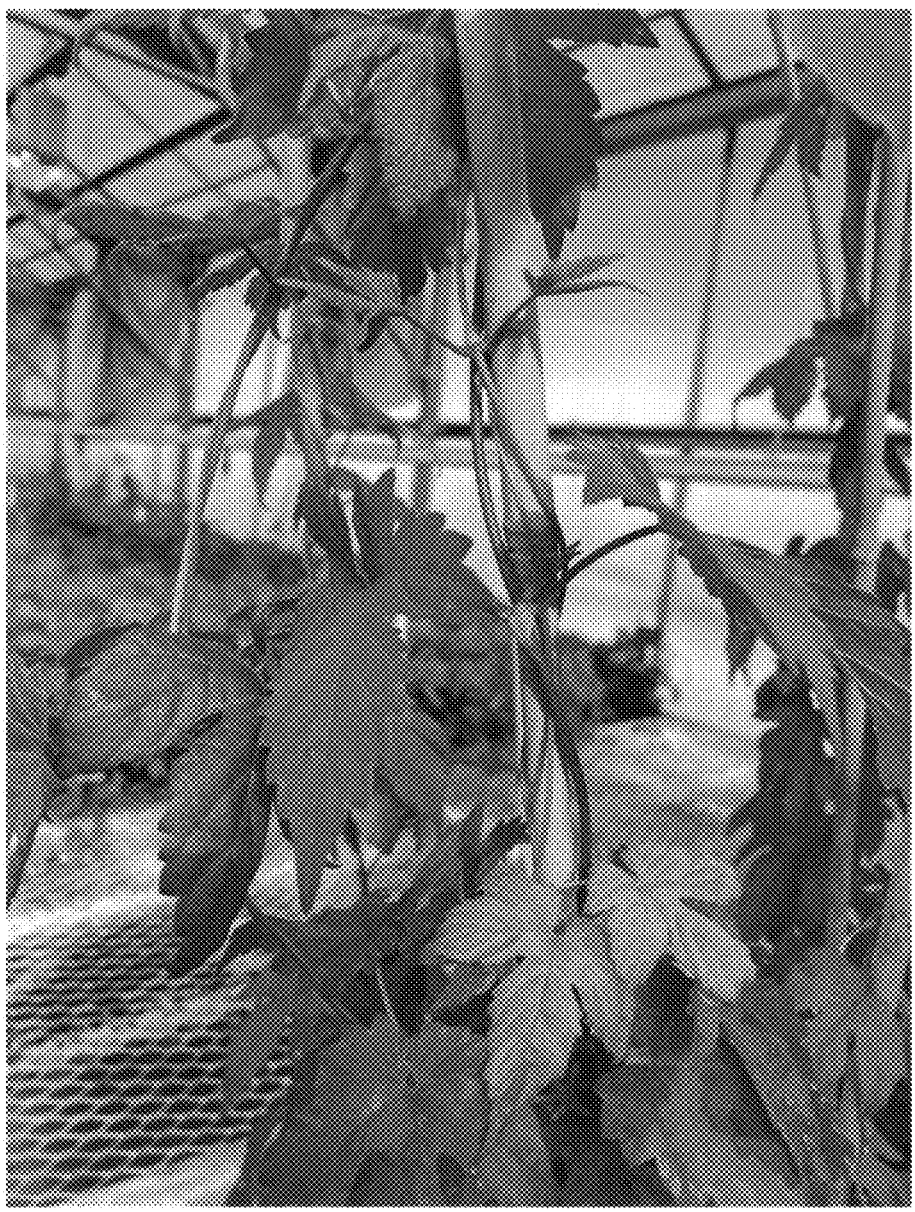
FIG. 1 illustrates a maturing 'HBC 695' hop plant at approximately three months of growth on a trellis.
Figure 2:
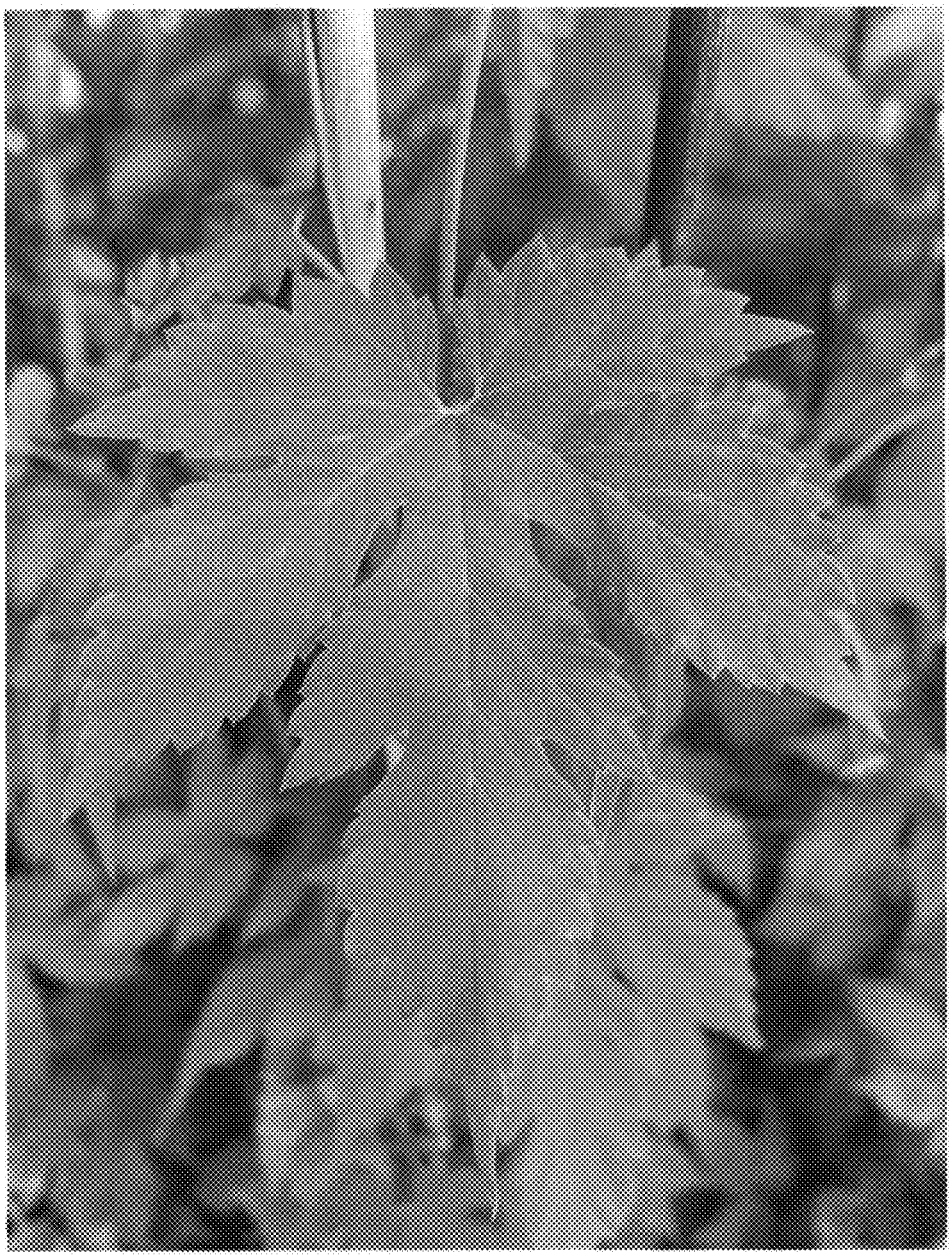
FIG. 2 illustrates a close up of leaves of a 'HBC 695' hop plant at approximately three months of growth.
Figure 3:
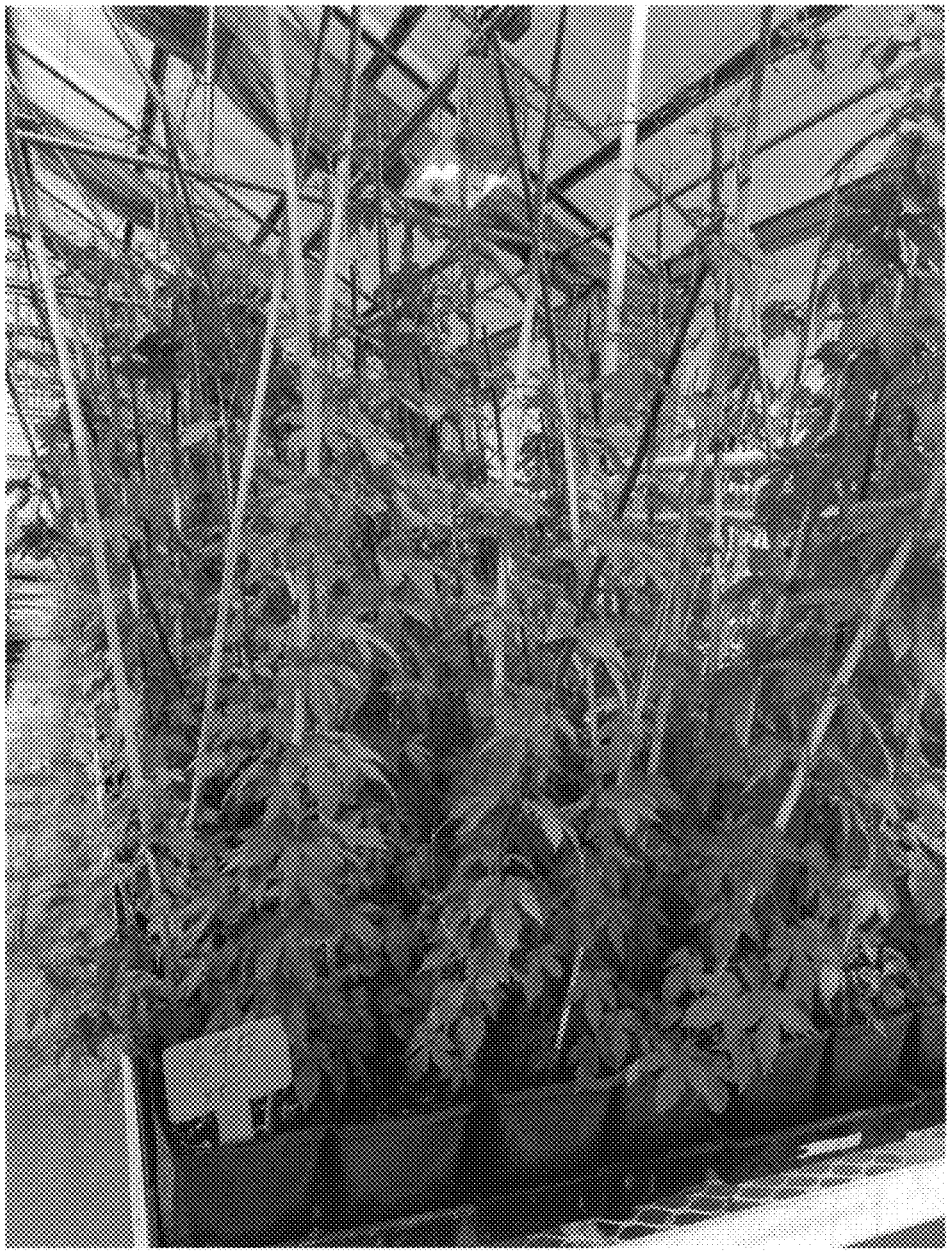
FIG. 3 illustrates a multiple of trellis with maturing 'HBC 695' hop plants at approximately three months of growth.
Figure 4:
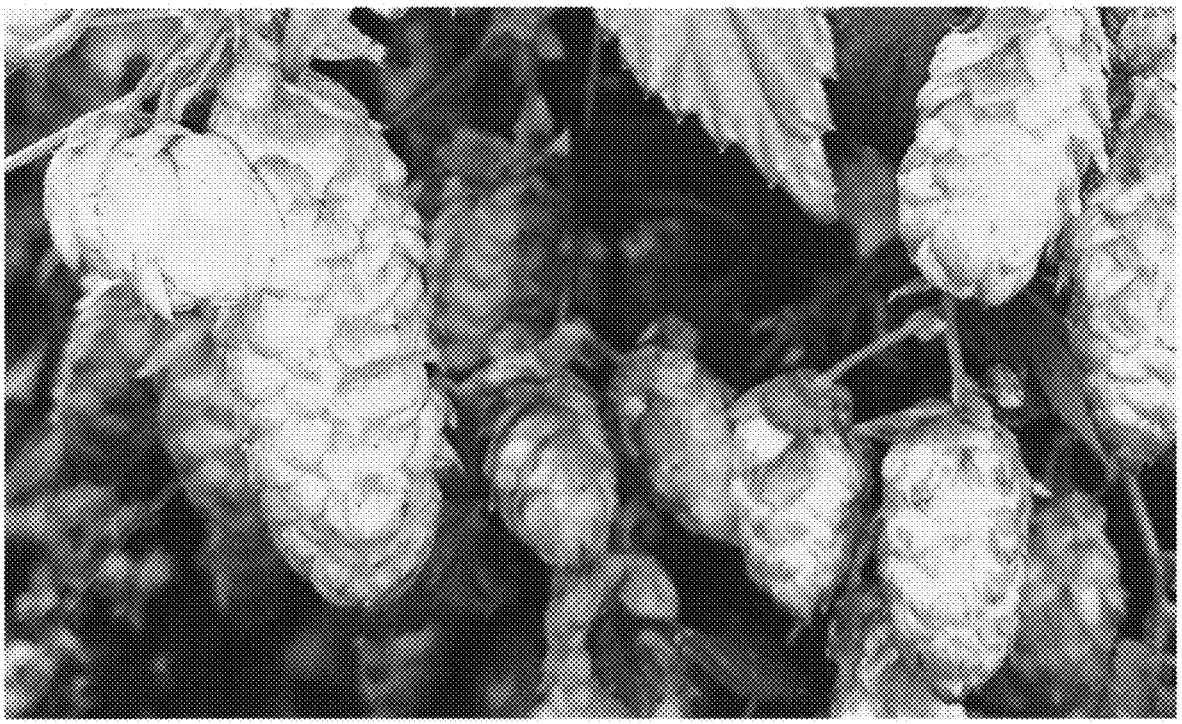
FIG. 4 illustrates the cones of a mature 'HBC 695' hop plant.
Figure 5:
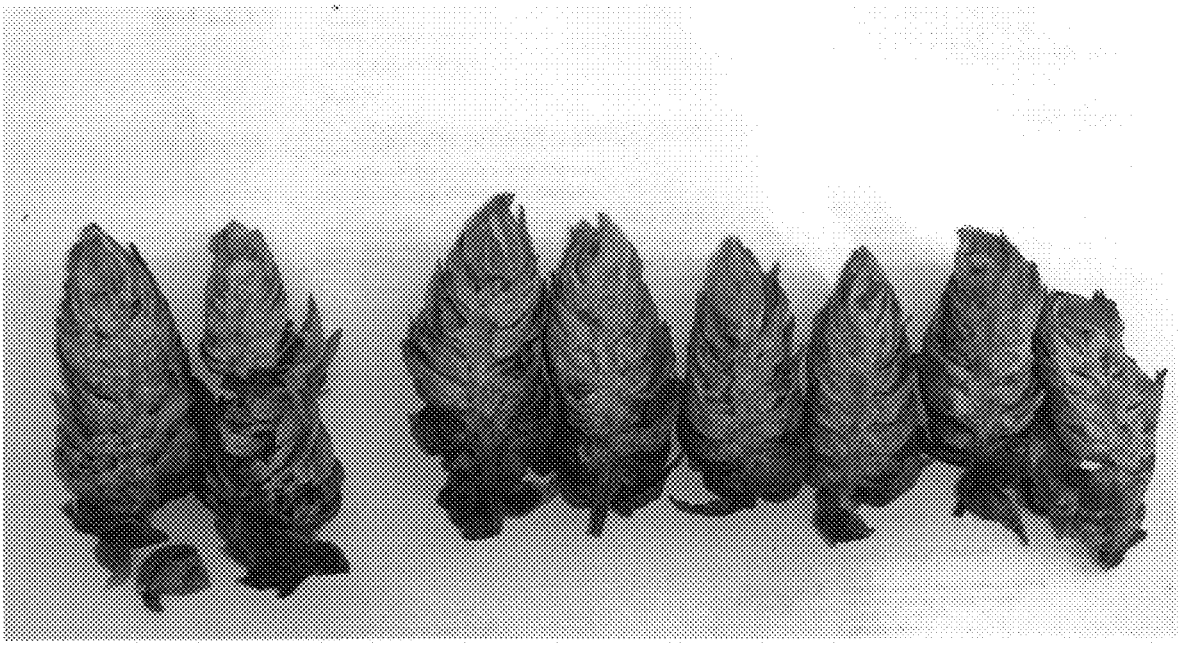
FIG. 5 illustrates cross-sections of mature cones of a 'HBC 695' hop plant.
Figure 6:
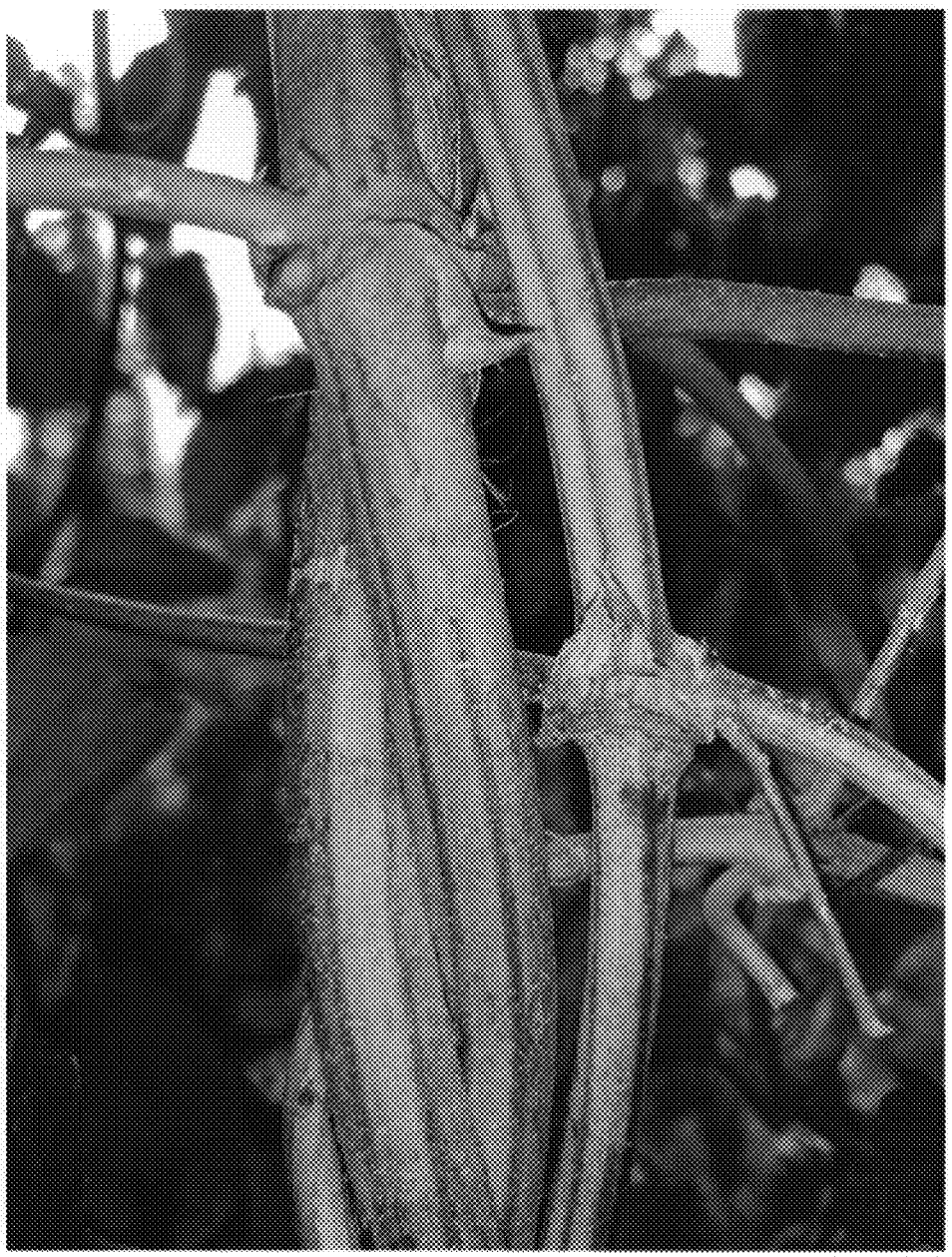
FIG. 6 illustrates a multiple of bines of a mature 'HBC 695' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made in February and August of 2020 at Granger, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. Color code designations are by reference to The R.H.S. Colour Chart, 4th ed., Copyright 2001, published by The Royal Horticultural Society of Great Britain.

Ploidy: Diploid.
Sex: Female.

Use: Brewing beer and ale.
Yield: Average yield is expected to be approx. 2,700 to 3,200 pounds per acre.
Plant shape: Cylindrical.
Growth type: Normal.
Disease and pest resistance or susceptibility:
*Powdery mildew* (*podosphaera macularis*).—Tolerant.
*Mites* (*tetranychus urticae*).—Tolerant.
Oil analytical characteristics (averages):

| | |
|---|---|
| % Alpha Acid (% cone weight) | 18 to 19 |
| % Beta Acid (% cone weight) | 4.3 to 4.6 |
| % Cohumulone (% alpha acids) | 22 to 23.5 |
| Total Oil (ml/100 g of cones): | 2.0 to 2.2 |
| Hop Storage Index (% loss) | 25.5 |

Bine:
*Bine color*.—Yellow-Green 144A.
*Stripe present*.—Yes.
*Stripe color*.—Red-Purple N57C.
*Stipule direction*.—Up.
*Stipule color*.—Yellow-Green 144A.
*Stipules per bine*.—36 to 60.
*Typical bine length*.—6 m to 7 m.
*Typical internode length on bine*.—19 cm to 25 cm.
*Typical internode length on lateral*.—9.5 cm to 15 cm.
*Bine diameter*.—11 mm at base; 11 mm at nine feet; and 10 mm at terminal end of eighteen feet.
*Average lateral length*.—76 cm to 112 cm.
*Lateral density at middle third of plant*.—Two Laterals per Node.
*Anthocyanin coloration on main bine*.—Weak.
Leaf:
*Arrangement*.—Opposite.
*Shape*.—Palmately Lobed.
*Apex*.—Acuminate.
*Margin*.—Serrated.
*Serrations per inch* (*typically*).—3 to 4.
*Pose*.—Up.
*Average length of mature leaf*.—12 cm to 13 cm.
*Average width of mature leaf*.—15 cm to 16 cm.
*Leaf blistering on the upper side of leaf blade*.—Absent.
*Color of mature leaf upper surface*.—Green 139A.
*Color of mature leaf lower surface*.—Green 139A.
*Color of immature leaf upper surface*.—Green 139A.
*Color of immature leaf lower surface*.—Green 139A.
*Number of lobes*.—3.
*Petiole color at base*.—Yellow-Green 146B.
*Average petiole diameter* (*mature*).—3 mm to 4 mm.
*Average petiole length* (*mature, typical*).—8.4 cm to 9.0 cm.
*Venation*.—Pinnate.
*Vein color*.—Yellow-Green 146B.
Cone:
*Cone shape*.—Oblong.
*Average cone length*.—4.5 cm.
*Average cone diameter*.—1.3 cm.
*Typical cone weight*.—1.10 g to 1.14 g.
*Bract shape*.—Obtuse.
*Bract base shape*.—Rounded.
*Bract margin*.—Entire.
*Bract tip shape*.—Apiculate.
*Bract tip position*.—Downward.
*Degree of bract opening*.—Closed.
*Bract tip color*.—Green N144A.
*Bract base color*.—Green N144A.
*Bract length*.—14 mm to 15 mm.
*Bract width*.—13 mm to 14 mm.
*Bracteole shape*.—Apiculate.
*Bracteole length*.—11 mm to 12 mm.
*Bracteole width*.—10 mm to 11 mm.
*Bracteole color* (*upper surface*).—Green N144B.
*Bracteole color* (*lower surface*).—Green N144B.
*Lupulin glands shape*.—Pedunculated Oblong Polyps.
*Number of lupulin glands per cone*.—Varies Greatly (Moderate to Many) with approximately 50,000 lupulin glands per Cone.
*Time of flowering*.—Mid to Late July.
*Maturity date range* (*early, medium, late*).—Medium.

The invention claimed is:

1. A new and distinct Hop plant as illustrated and described herein.

* * * * *